United States Patent
Levy (10) Patent No.: US 12,144,761 B1
(45) Date of Patent: Nov. 19, 2024

(54) CAST INFLATABLE BLADDER LINER

(71) Applicant: Peter L. Levy, San Francisco, CA (US)

(72) Inventor: Peter L. Levy, San Francisco, CA (US)

( * ) Notice: Subject to any disclaimer, the term of this patent is extended or adjusted under 35 U.S.C. 154(b) by 0 days.

(21) Appl. No.: 18/654,365

(22) Filed: May 3, 2024

(51) Int. Cl.
*A61F 5/058* (2006.01)

(52) U.S. Cl.
CPC .................... *A61F 5/05816* (2013.01)

(58) Field of Classification Search
CPC ........ A61F 5/05816; A61F 5/058; A61F 5/05; A61F 5/01; A61F 5/00
See application file for complete search history.

(56) References Cited

U.S. PATENT DOCUMENTS 3,701,349 A * 10/1972 Larson ................ A61F 5/05816
602/14

FOREIGN PATENT DOCUMENTS

WO WO-9310732 A1 * 6/1993 ........... A61F 13/041

* cited by examiner

*Primary Examiner* — Tarla R Patel
(74) *Attorney, Agent, or Firm* — Walt Froloff (57) ABSTRACT

An cast inflatable bladder liner providing air-flow and massage over a fractured limb is introduced to eliminate itching, infection, moisture and bacterial buildup on an injured limb. Fluctuating air-pressure nipples on the bladder-skin surface promote massaging the skin while also ventilating the injury during cast placement. Air pressure is sourced by manual bulb squeezing or electrical power to mechanical pump on demand pressured air. The inflatable bladder has 4 edges and 2 sides and controlled valves for providing two modes of operation, one which provides air-tight seals in static mode and another mode which allows for air-flow over the skin surface.

14 Claims, 5 Drawing Sheets

CAST INFLATABLE BLADDER LINER

BACKGROUND

Field of the Invention

The present invention relates generally to cast lining and more specifically, to skin ventilating and massaging bladder cast lining for appendage immobilization required bone mending duration.

Background of the Invention

There are several methods used for lining casts for broken appendages, such as arms or legs. Some of the common methods include cotton padding, gauze, stockinette, Plaster of Paris, fiberglass, waterproof cast liners, and padding replacements.

Using cotton padding, a layer of soft cotton padding is placed directly on the skin before applying the cast material. This padding helps to provide cushioning and prevent irritation. A stockinette layer or tubular bandage is typically placed over the cotton padding. This helps to protect the skin and provides a smooth surface to secure the cast material. Plaster of Paris is a traditional casting material that is mixed with water to create a thick paste which is applied over the stockinette and shaped to form the cast. Once it hardens, this configuration provides rigid support for the broken bone.

Fiberglass casting tape is another common material used for casts. It is lighter and more durable than plaster of Paris and can be applied directly over the stockinette. Some modern casts come with waterproof liners that allow patients to bathe or swim without getting the cast wet. These liners are typically made of materials like Gore-Tex or polyethylene.

The choice of lining material depends on factors such as a patient's comfort, the type and location of the fracture, and the duration of cast immobilization. Few lining material lasts the healing period where circumstances are even at their best, so at times padding replacements are required to reset and refresh the cast. Newer materials, such as synthetic padding or foam, are used as alternatives to traditional cotton padding. These materials are lightweight, breathable, and less likely to cause skin irritation.

Skin irritation from long-term cast use can be caused by several factors, among them friction, moisture, pressure, allergic reaction, poor hygiene and skin breakdown.

Friction can arise from cast rubbing against the skin can leading to irritation, especially if the cast is not properly padded or if the skin is sensitive. Moisture can build up inside the cast, either from sweat or water exposure. This can soften the skin and make it more prone to irritation. Excessive pressure exerted by the cast on the skin can cause pressure sores, especially if the cast is too tight or if the patient is immobile for long periods.

Skin irritation can also arise from allergic reactions: Some develop allergic reactions to the materials used in the cast, such as latex or certain types of padding. Moreover, inadequate cleaning and drying of the skin under the cast can lead to bacterial or fungal infections, which can cause further irritation. Also prolonged pressure and friction can lead to skin breakdown, which can manifest as redness, blisters, or even open sores.

What is needed are appendage cast liners that keep the skin under the cast clean and dry, avoid itching from inserting objects inside the cast to scratch the skin, and allow for medical attention if any signs of irritation or infection develop. What are also needed are simple cast linings or wrapping bandages for sufficient periods of cast application without resetting lining or padding material due to skin irritation.

Some solutions have been attempted with inflatable bladders. One such included top layer and a bottom layer with an inflatable bladder of smaller dimension positioned there between, an interiorly positioned pocket for insertion of a gel pack and a hand-bulb for increasing the pressure within the bladder and thereby applying pressure to the gel pack. A release valve was incorporated into the bulb for selectively releasing the bladder pressure.

In another invention, a compress having a plurality of layers of absorbent material on one side and a rubber lining on the other side was tried. The lining having a longitudinal seam along the bottom and two seams extending upwardly to unite the several layers of materials along the seams and form a pocket was made such that the pocket would be capable of receiving ice or water.

In yet another solution a form of a wrap for use as a cold compress, preferably on the legs of horses. The wrap included a layer of highly compressed absorbent material, such as artificial sponge, a resilient net-like supportive backing sewn thereto and with a tongue extending from one end thereof, with the wrap held in place on the leg. A fine net-like supportive backing was to promote rapid evaporation by allowing maximum exposure of the water to the atmosphere, thus cooling the horse's leg.

In other innovations, cold treatment devices are available with a variety of cooling and compressing means including for example endothermic chemical packs and ice packs which may be in place with elastic bandages and elaborate refrigerated water circulation. None of these temperature related solutions keep the skin from the typical irritations mentioned above.

Some bone fracture treatment remedies have been attempted with inflatable bladders. One such included top layer and a bottom layer with an inflatable bladder of smaller dimension positioned there between, an interiorly positioned pocket for insertion of a gel pack and a hand-bulb for increasing the pressure within the bladder and thereby applying pressure to the gel pack. A release valve was incorporated into the bulb for selectively releasing the bladder pressure.

In another invention, a compress having a plurality of layers of absorbent material on one side and a rubber lining on the other side was tried. The lining having a longitudinal seam along the bottom and two seams extending upwardly to unite the several layers of materials along the seams and form a pocket was made such that the pocket would be capable of receiving ice or water.

In other innovations, cold treatment devices are available with a variety of cooling and compressing means including for example endothermic chemical packs and ice packs which may be in place with elastic bandages and elaborate refrigerated water circulation. None of these temperature related solutions keep the skin from the typical irritations mentioned above.

According to the Centers for Disease Control and Prevention (CDC), there were approximately 6.3 million fractures in the United States in 2019. This includes fractures from all causes, such as falls, sports injuries, and car accidents. The number of fractures can vary from year to year based on factors such as population growth, changes in behavior (e.g., more or fewer people participating in sports), and improvements in safety measures.

The treatment for fractures varies depending on the type and severity of the fracture. However, casting is a common treatment for many types of fractures, particularly those that are stable and do not require surgical intervention. In general, for fractures that can be managed non-surgically, such as certain types of wrist, arm, and leg fractures, a cast or splint is often prescribed to immobilize the bone and allow it to heal properly. Casts take time to create as each must be done in custom individual fashion. What are needed are casts that can snap on quickly yet still be uniquely fitting.

Where casts are used, the problems of keeping the skin clean, itch and infection free arise even with the current practices of using casts a part of treatment for fractures. Over time muscles atrophy and shrink, leaving the cast with too much play and non-supportive. In many cases this indicates cast removal, cleaning the skin and re-application of a fresh cast.

What is needed are cast linings that don't require insertion of a gel pack and a hand-bulb for increasing the pressure within a bladder for cooling and applying pressure to a gel pack as these do not solve the problem of skin irritation, bacterial growth and restriction of blood flow. What is needed are ways to keep stable pressure on the break, while allowing massage and aeration of the skin surface under the caste. What is needed are ways to reduce or eliminate cast friction, moisture, pressure, allergic reaction, poor hygiene and skin breakdown.

SUMMARY

The present invention discloses an inflatable bladder cast liner made from four edges and two sides, adapted for wrapping around a fractured limb for a cast liner. The cast liner has main inflatable bladder four edges, two circumferential edges for wrapping about an adaptive appendage axis and two longitudinal edges extending a length of the adapted appendage surface parallel with the adapted appendage axis.

The two longitudinal edges are coupled to and bind the main bladder having two surface sides, a cast side and an adapted appendage adjacent side. Each of the bladder two longitudinal edges have mating connectors extending parallel to the adapted appendage axis for coupling the inflatable bladder air-tightly about a more-or-less tapered cylindrical adapted appendage surface. The two circumferential edges, are wrapped about the adapted appendage axis, forming an air-tight bladder, each circumferential edge coupled to the main inflatable bladder forming an adjustable air-tight seal with the adapted appendage surface. The main inflatable bladder adapted appendage surface side have an array of nipples protruding from the main bladder adapted appendage adjacent side toward and in contact with the adapted appendage surface.

One longitudinal edge may also have an separate inflatable bladder wrapped about the adapted appendage axis forming an adjustable air-tight seal at that longitudinal edge. An external air pump coupled with flexible tubing to the main and circumferential edge inflatable bladders provide pressurized air to the main and circumferential edge bladders. An external air pump mode switch controller for directing air flow to either the main inflatable bladder or at both the main inflatable bladder and at least one circumferential edge bladder, whereby the inflatable bladders working in concert with the air pressure controller provide bladder air for static pressure stabilizing the cast and also adjustably for air ventilation over the appendage skin selectably.

BRIEF DESCRIPTION OF DRAWINGS

Specific embodiments of the invention will be described in detail with reference to the following figures.

DETAILED DESCRIPTION

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

OBJECTS AND ADVANTAGES

An object of the invention is to provide a quick application cast liner where otherwise the need for removing and replacing spent gauze is no-longer necessary, to eliminate inflammation pain or irritate to the surrounding skin or wound.

Another object of the invention is to eliminate skin irritation from allergic reactions caused by a caste.

Yet another object of the invention is eliminate the use of allergic reactions due to the materials used in the cast, such as latex or certain types of padding.

Another object to the invention is to reduce or eliminate the need for cleaning and drying of the skin under the cast which can lead to bacterial or fungal infections.

Yet another object of the invention is to prevent prolonged pressure and friction which can lead to skin breakdown, manifesting as redness, blisters, or even open sores.

Another object of the invention is to provide appendage cast liners that keep the skin under the cast clean and dry, preventing the need for inserting objects inside the cast to scratch the itching skin, and allow for medical attention if any signs of irritation or infection develop.

Yet another object of the invention is to provide simple and easy to use cast linings or wrapping bandages for sufficient periods of cast application without resetting lining or padding material due to skin irritation.

Another object of the invention is to massage the skin under a cast to provide normal aeration and good blood flow on the skin.

Specific embodiments of the invention will be described in detail with reference to the following figures.

Figure 1:
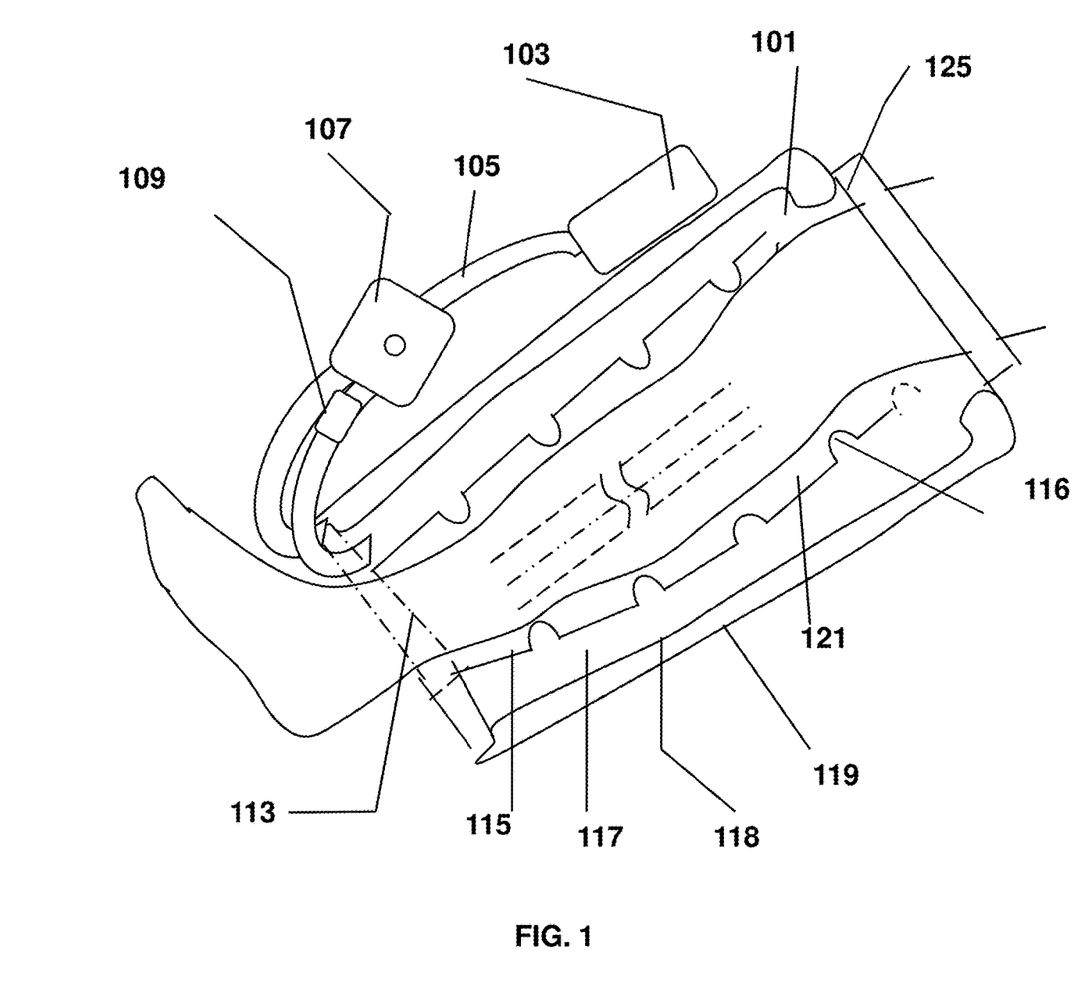
FIG. 1 illustrates a cast bladder liner for a broken bone in an embodiment of the invention.

FIG. 1 illustrates a cast 119 on a bladder liner for a broken bone in an embodiment of the invention.

A view of a leg cast 119 with cross sectional view of a cast liner internals is schematically represented. A bladder-like 117 liner that inflates where necessary to hold a cast 119 firm and supportive with allowance for leg mass atrophy and shrinkage is shown. A pump 103 serves to inflate a bladder 117 on demand to convect air by an appendage surface to dry it and take out excess moisture, bacteria and odor buildup.

In an embodiment of the invention a flat-like inflatable bladder 117 with four edges and two sides, adapted for wrapping around a fractured limb as a cast 119 liner. The four edge bladder has two circumferential edges 125 113 and two longitudinal edges, the longitudinal edges for extending a length parallel with the appendage axis and covering the adopted appendage surface. The two longitudinal edges are coupled to and bound the bladder 117 with an air-tight seal, and forming a bladder with two sides, a cast side 118 and an adapted appendage adjacent side. Each of the bladder two longitudinal edges have a mating connector to the opposite longitudinal edge, extending in parallel to the appendage axis for coupling the bladder 117 air-tightly around a more-or-less tapered appendage surface. The two circumferential edges, circumferential edge1 125 and circumferential edge2 113, form an air-tight bladder coupling seal for wrapping the inflatable bladder around the adapted appendage. The inflatable bladder 117 appendage surface side 115 has an array of nipples protruding from the bladder 117 adapted appendage side 115 toward and in contact with the adapted appendage surface. The longitudinal edge 1 is contiguous with and coupled to an inflatable tube-like bladder forming an adjustable air-tight seal when wrapped around an adapted appendage with the inflatable bladder liner.

An external air pump 103 is serially coupled with a mode switch 107 via flexible tubing 105 for providing pressurized air selectable to the main inflatable bladder 117 and circumferential edsge2 bladder 113. The mode switch controller provides the option to inflate the main inflatable bladder 117 and circular edge2 sealing bladder for static cast 119 support or optionally air-flow through the main bladder ventilating the adapted fractured limb surface-main bladder 117 inside surface 115 gap 121 and exiting a deflated circular edge2 bladder 113 seal. The ventilation option pressurizes the nipple array 116 to provide a gap 121. The inflatable bladders 117 113 working in sync or concert with the air flow controller 107 provide pressured air for static pressure stabilizing the cast and also adjustably for air ventilation over the fractured limb skin 121 adjustably.

In an embodiment of the invention a switch 107 with a flutter valve 109 serially coupled to the selector controller to provide automatically fluctuating main inflatable bladder air-flow to ventilate and massage the appendage surface during appendage skin aeration or flow-through mode.

Figure 2:
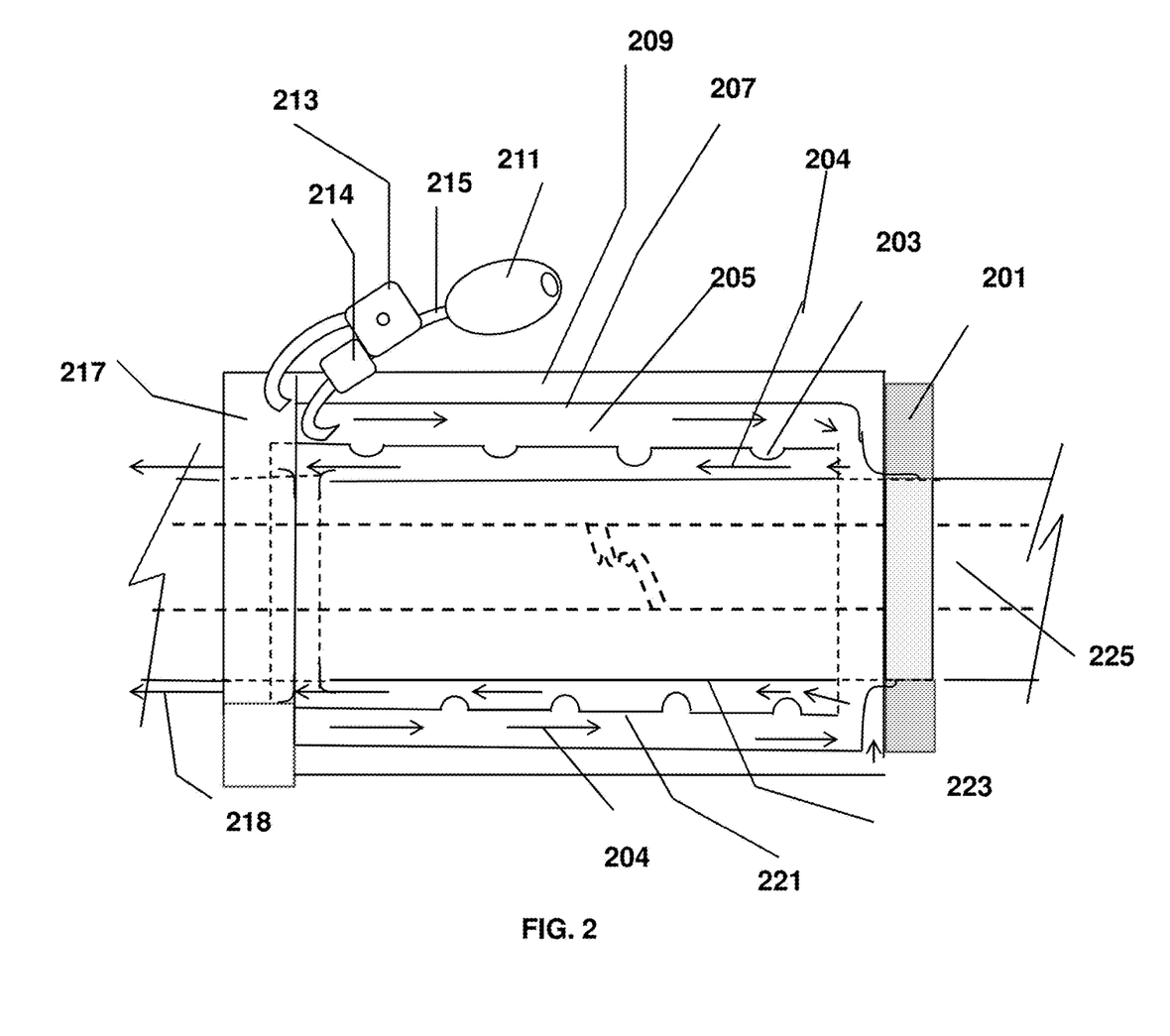
FIG. 2 shows the air flow modes for a cast bladder liner in an embodiment of the invention.

FIG. 2 shows the air flow modes for a cast bladder liner in an embodiment of the invention. In an embodiment of the invention a switch 213 with a flutter valve 214, the flutter valve provide main inflatable bladder fluctuating air-flow 204 pressure to ventilate and massage the adapted appendage skin.

A bandage where the pressure on the skin can alternate is desirable in order to prevent pressure sores. In an embodiment of the invention this is done through mode selection switch 213 controlling fluctuating pressure to a wrap-around bladder cast liner composed of rubber or nitrile material. An appendage, wrapped by the inflatable bladder sourcing fresh air by a manual pump bulb 211 or electric pump across the appendage surface skin 223 under varying pressure. The bladder surface 221 that touches the skin 223 has a series of nipples 203 that inflate as the bladder air pressure increases and drives fresh air 204 displacing the moisture and any bacterial growth on the appendage surface 223 having a reduced pressure to provide flow through. In an embodiment the bulb pump 211 may have a shuttle device which when squeezed closes and then again opens by attaching a compressors to the flexible tube 215 or the hand-pump bulb 211 can be squeezed manually from time to time. By varying the pressure on the appendage skin 223 blood flow is enhanced and pressure sores can be eliminated. In a disposable cast 209 embodiment the cast 209 is removed and the air bladder liner is destroyed and disposed. In another embodiment a cast 209 is put on a layer of gauze typically wrapped around the appendage, a thin layer of gauze is wrapped around the bladder and then the cast 209 is applied. The bulb can be a typical hand pump as used with blood pressure measuring cuffs.

In an embodiment a main inflatable bladder 205 with four edges and two sides adapted for wrapping around a fractured limb 225 as a cast 209 liner. Two circumferential edges 201 217 are for wrapping about an adaptive appendage axis and the two longitudinal edges are extended a length of the adapted appendage surface parallel with the adapted appendage axis. The two longitudinal edges are coupled to and bound the main bladder 205 having two surface sides, a cast side 207 and an adapted appendage adjacent or skin side. Each of the bladder two longitudinal edges come with mating connectors extending parallel to the adapted appendage axis for coupling the inflatable bladder air-tightly about a more-or-less tapered cylindrical adapted appendage surface 223.

The two circumferential edges, circumferential edge1 217 and circumferential edge2 217, are wrapped about the adapted appendage axis, forming an air-tight main bladder 205. The longitudinal edge1 201 contiguous with and coupled to an inflatable bladder 205 wrapped about the adapted appendage axis forming an adjustable air-tight seal at the longitudinal edge1 201. Each circumferential edge is coupled to the main inflatable bladder 205 forming an adjustable air-tight seal with the adapted appendage surface 223 at the static or stable pressure option. The main inflatable bladder 205 adapted appendage surface side 221 has an array of nipples 203 protruding from the main bladder 205 adapted appendage adjacent side 221 toward and in contact with the adapted appendage surface 223.

An external air pump 211 is coupled to the main 205 and circumferential edge1 bladder 217 with flexible tubing 215 to the main and circumferential edge1 inflatable bladders providing pressurized air 204 to the main 205 and circumferential edge1 217 bladders. The pump can be manual or electrical powered and is coupled to a selectable mode switch controller 213 for directing air flow to either the main inflatable bladder 205 or at both the main inflatable bladder 205 and at least one circumferential edge bladder 217. Thus the modes switch provides air flow 204 through 218 for air ventilation over the appendage skin or for static pressure bladder pressure stabilizing the cast blocking through air-flow 218 via inflation of the circumferential edge 1 bladder creating a seal with the appendage surface skin 223.

Figure 3:
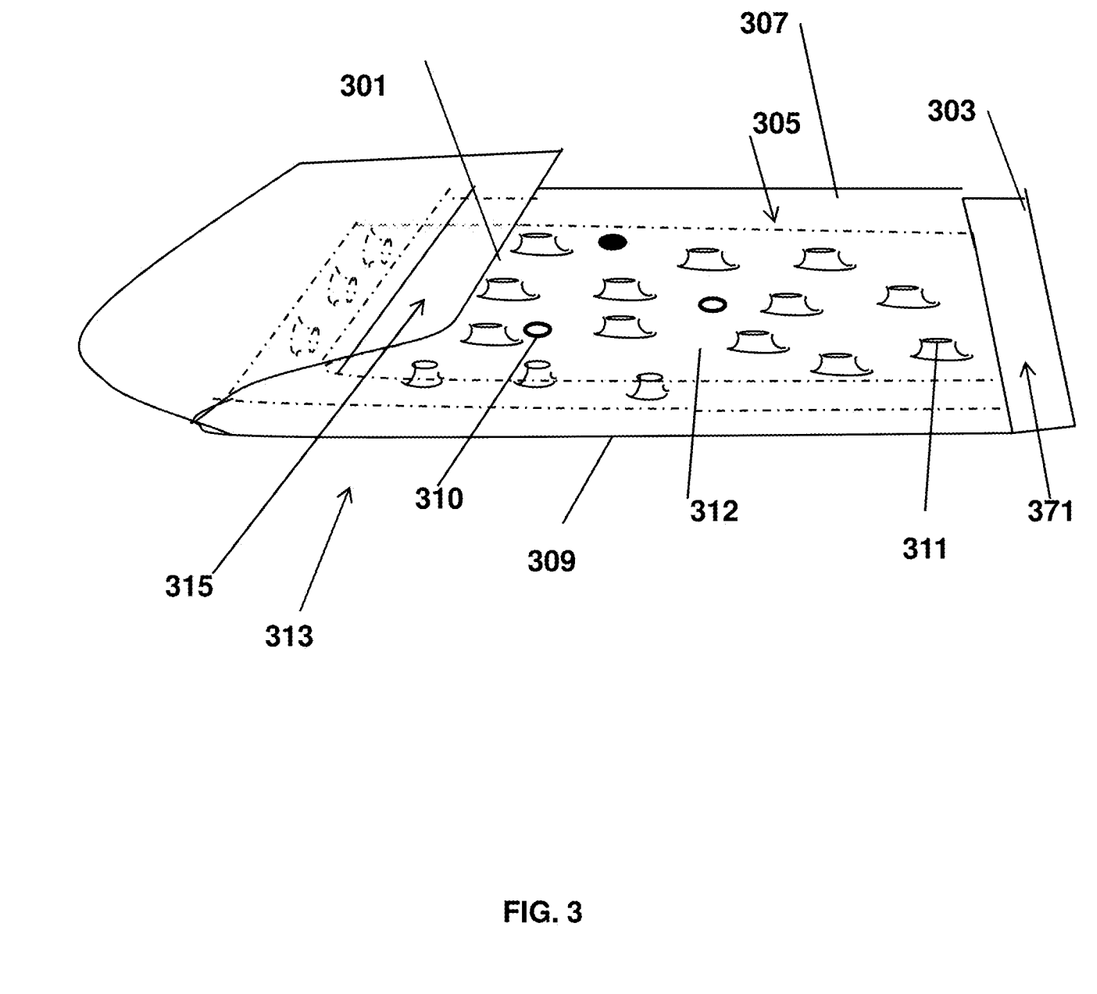
FIG. 3 illustrates a cast liner bladder geometry and bladder inside with a nipple array in an embodiment of the invention.

FIG. 3 illustrates a cast liner bladder geometry and bladder inside, appendage adjacent, surface with a nipple array 311 in an embodiment of the invention.

In another embodiment a flat-like inflatable bladder 313 layout is shown with four edges 301 303 307 309 and two sides, is adapted for wrapping around a fractured limb as a cast liner. This embodiment has two circumferential edges 307 309 adapted for wrapping an appendage surface having and two longitudinal edges 301 303 extending a length of the adapted appendage surface parallel with the appendage axis, the two longitudinal edges coupled to and bounding a bladder 313 having two sides, a cast side and an appendage adjacent side with a nipple array 311. Each of the bladder two longitudinal edges 301 303 with mating connectors 315

317 extending in parallel to the appendage axis for coupling the bladder 313 air-tightly around a more-or-less tapered appendage surface.

The two circumferential edges, circumferential edge 1 307 and circumferential edge2 309 are wrapped around the adapted appendage axis, forming an air-tight bladder, each circumferential edge coupled to the bladder forming an adjustable air-tight seal for wrapping an inflatable bladder liner to the adapted appendage. The two circumferential bladder edge mating connectors can be made from hook and loop, tongue and strap, button, elastic hook-ring, belt and snap-on.

The inflatable bladder 313 appendage side has an array of nipples 311 protruding from the bladder adapted appendage side 312 toward and in contact with the adapted appendage surface. The longitudinal edge1 307 is contiguous with and coupled to an inflatable tube-like bladder 305 wrapped around an adapted appendage axis forming an adjustable air-tight seal. In another embodiment the inflatable bladder 313 adapted appendage surface side 312 has an array of perforations 310 on the main bladder adapted appendage adjacent side 312 with the adapted appendage surface.

Figure 4:
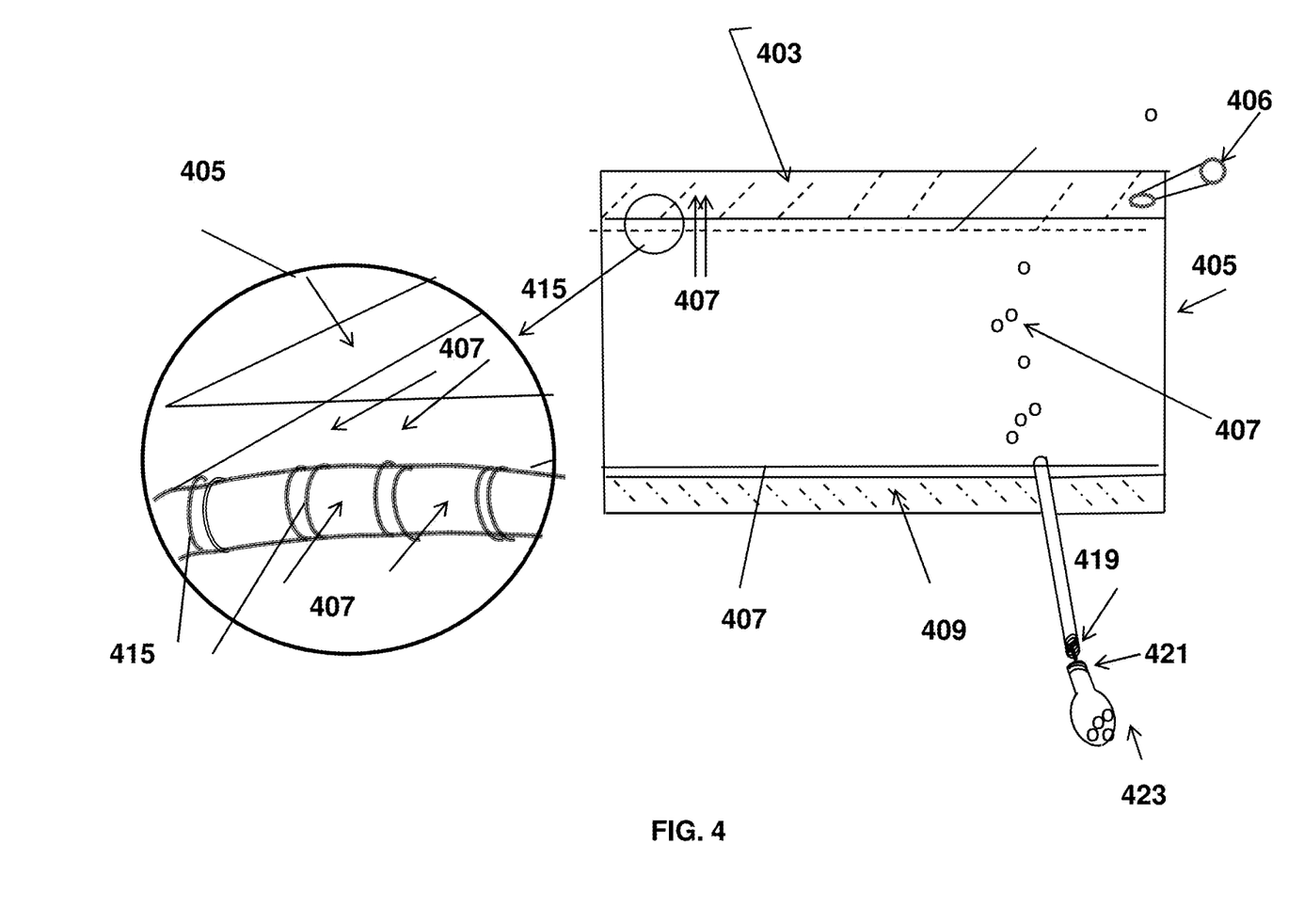
FIG. 4 shows a cast liner bladder edge lip bridge for channeling air to the bladder skin side on in an embodiment of the invention.

FIG. 4 shows a cast liner bladder edge lip bridge 415 for channeling air 407 to the main bladder 405 skin side on in an embodiment of the invention.

The circumferential edge1 401 is shown with an edge lip bridge 415 which provides a small separation from the main bladder 405 over appendage skin to provide bladder air flow 407 through an adapted appendage-skin gap opening produced by the bladder adapted appendage side inflated nipples and air pressure. A circumferential edge bladder 403 acts in concert with the lip bridge 415 to allow or constrict air flow at the circumferential Edge1. In another embodiment of the invention the main bladder 405 nipple surface have pressure dropping array of air openings apart from the nipples to provide skin aeration with or without a lip bridge as well. Pressurized air for the main bladder 405 comes via flexible tube 419 serially with a control valve 421 sourced by external pump 423, selectably manual bulb or electrical. The circumferential edge constraint 409 is air-tight seal of neoprene, rubber, or other flexible fluid impervious material.

Figure 5:
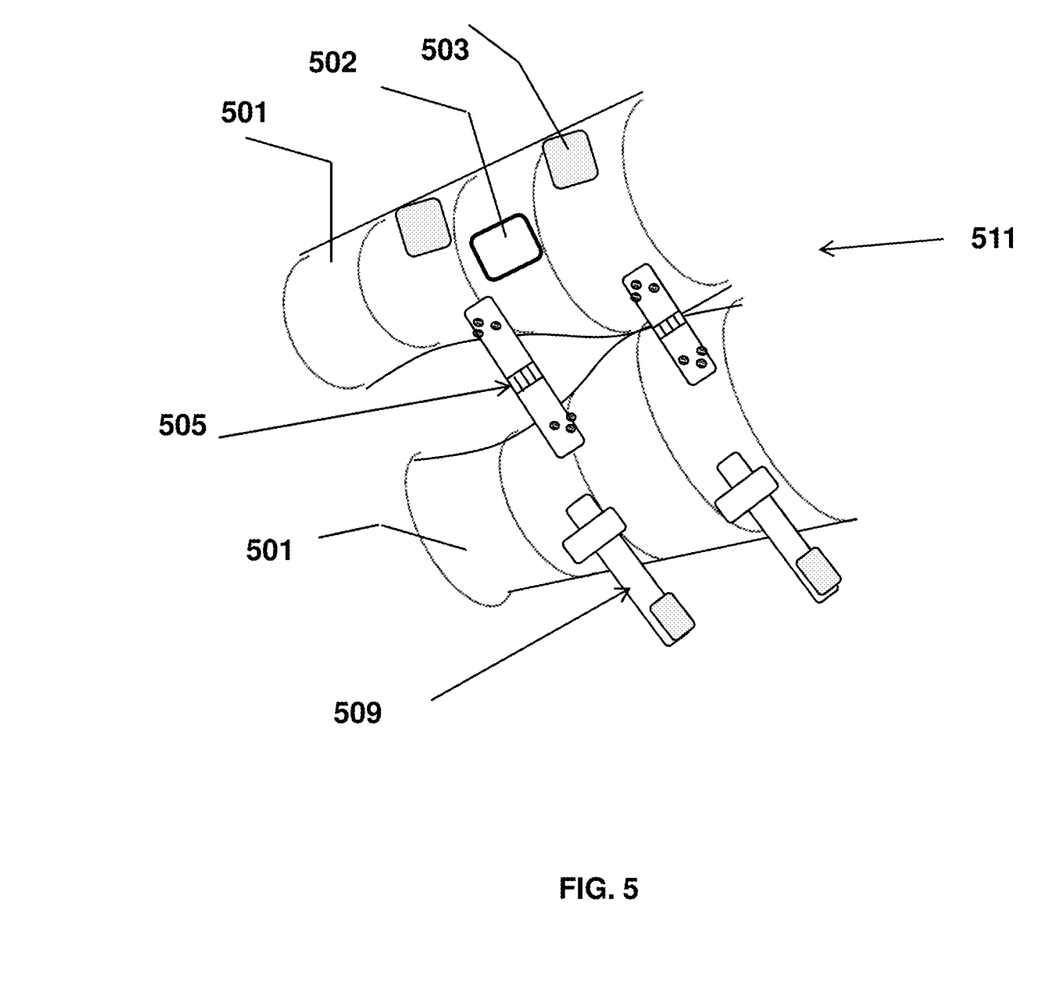
FIG. 5 illustrates a field deployable fast installing cast shell for a cast bladder liner in an embodiment of the invention.

FIG. 5 illustrates a field deployable fast installing cast shell for a cast bladder liner in an embodiment of the invention. Any typical or conventional cast can be used with the invention liner but a fast installing pre-made cast 511 can be fitted with the invention liner as well. The inflatable bladder liner lends itself to be adjustable by controlling air pressure to transfer appendage support from a cast to a broken appendage that is set properly for healing. A pre-made fast installing cast 511 is shown to have complementary half shells 501 attached by half cast hinges 505 at one coupling and with separate half cast coupler 509 to adjust the two complementary cast halves into one cohesive cast support.

Thus a field cast 511 of pre-made complementing cast halves 501 coupled to the inflatable bladder liner, cast halves using hinge 505, belt 509 and buckle 503 mating connector coupling and can be deployed with the invention inflatable liner. Pre-made fast installing cast material cab be made from a set of materials including fiberglass, stockinette, Plaster of Paris, polyethylene, synthetic foam, and composite. Some fast install pre-made cast embodiments material may have include a transparent window 502 material as well. Material can also come from organic or synthetic padding or foam, traditional cotton, lightweight, breathable material.

Therefore, while the invention has been described with respect to a limited number of embodiments, those skilled in the art, having benefit of this invention, will appreciate that other embodiments can be devised which do not depart from the scope of the invention as disclosed herein. Other aspects of the invention will be apparent from the following description and the appended claims.

What is claimed is:

1. An inflatable bladder cast liner comprising: a main inflatable bladder with four edges and two sides, adapted for wrapping around a fractured limb as a cast liner; the main inflatable bladder comprising four edges, two circumferential edges configured for wrapping about the fractured limb axis and two longitudinal edges configured to extend about a length of the fractured limb skin parallel with the fractured limb axis; the two longitudinal edges coupled to and bounding the main bladder having two surface sides, a cast side and the fractured limb adjacent side; each of the inflatable bladder two longitudinal edges with mating connectors extending parallel to the fractured limb axis for coupling the inflatable bladder air-tightly about a more-or-less tapered cylindrical the fractured limb skin; the two circumferential edges, circumferential edge 1 and circumferential edge2, wrapped about the fractured limb axis, forming an air-tight bladder, each circumferential edge coupled to the main inflatable bladder forming an adjustable air-tight seal with the fractured limb skin; the main inflatable bladder having the fractured limb skin side having an array of nipples protruding from the main bladder fractured limb adjacent side toward and in contact with the fractured limb skin; the longitudinal edge 1 contiguous with and coupled to an inflatable circumferential edge bladder wrapped about the fractured limb axis forming an adjustable air-tight seal at the longitudinal edge 1; an external air pump coupled with flexible tubing to the main inflatable bladder and circumferential edge1 inflatable bladders providing pressurized air to the main and circumferential edge1 bladders; an external air pump mode switch controller for directing air flow to either the main inflatable bladder or at both the main inflatable bladder and at least one circumferential edge bladder, the external air pump mode switch controlling a flutter valve automatically fluctuating main inflatable bladder air-flow to ventilate and massage the fractured limb skin; whereby the main inflatable bladders working in sync with the air pressure controller provide bladder air for static pressure stabilizing a cast and also adjustably for air ventilation over the fractured limb skin selectably.

2. The inflatable bladder cast liner as in claim 1 wherein the two circumferential bladder edge mating connectors are hook and loop, tongue and strap, button, elastic hook-ring, belt and snap-on.

3. The inflatable bladder cast liner as in claim 1 further comprising the pump mode which is either manual or electrical powered.

4. The inflatable bladder cast liner comprising as in claim 1 further comprising a pair of pre-made complementing cast halves coupled to the inflatable bladder cast liner, cast halves using hinge, belt and buckle mating connector coupling.

5. The inflatable bladder cast liner as in claim 1 wherein cast material are from a set of materials including fiberglass, stockinette, Plaster of Paris, polyethylene, synthetic foam, and composite.

6. The inflatable bladder cast liner as in claim 1 further comprising the circumferential edge2 with an edge lip bridge for providing bladder air flow to enter the fractured limb skin gap produced by the inflatable bladder fractured limb side inflated nipples.

7. The inflatable bladder cast liner as in claim 1 further comprising the inflatable bladder the fractured limb skin with an array of perforations on the main bladder fractured limb adjacent side with the fractured limb skin.

8. A method for an inflatable bladder cast liner comprising the steps of: providing an inflatable bladder with four edges and two sides, wrapped around an fractured limb for a cast liner; providing the inflatable bladder with two circumferential edges for an fractured limb skin surface with and two longitudinal edges extending a length of the fractured limb skin parallel with the fractured limb axis, the two longitudinal edges coupled to and bounding a bladder having two sides, a cast side and an adapted for fractured limb adjacent side; coupling each of the bladder two longitudinal edges with mating connectors extending in parallel to the fractured limb axis for coupling the inflatable bladder air-tightly around a more-or-less tapered fractured limb skin; wrapping the two circumferential edges, circumferential edge 1 and circumferential edge2, around the fractured limb axis, forming an air-tight bladder, each circumferential edge coupled to the bladder forming an adjustable air-tight seal for the inflatable bladder liner; providing an array of nipples protruding from the bladder fractured limb side toward and in contact with the fractured limb skin; coupling the longitudinal edge1 contiguous with an independently controlled inflatable tube-like bladder wrapped around the fractured limb axis forming an adjustable air-tight seal; providing an external air pump serially coupled with flexible tubing for connecting pressurized air to the main and circumferential tube bladders independently; providing an external air pump switch controller for air flow to at least two inflatable bladders, the main bladder and the circumferential edge1 tube bladder; providing the switch control with a flutter valve automatically fluctuating main inflatable bladder airflow to ventilate and massage the adapted fractured limb skin,
   whereby the inflatable bladders working in sync with the air pressure controller provide bladder air for static pressure bladder stabilizing the cast and also adjustably for ventilation over the fractured limb skin on demand.

9. The method for an inflatable bladder cast liner as in claim 8 wherein the two circumferential bladder edge mating connectors are hook and loop, tongue and strap, button, elastic hook-ring, belt and snap-on.

10. The method for an inflatable bladder cast liner as in claim 8 further comprising the step of providing the pump which is manual or electrical powered.

11. The method for an inflatable bladder cast liner as in claim 8 further comprising the step of providing a pair of pre-made complementing cast halves coupled to the inflatable bladder liner, cast halves using hinge, belt and buckle mating connector coupling.

12. The method for an inflatable bladder cast liner as in claim 8 wherein cast material are from a set of materials including fiberglass, stockinette, Plaster of Paris, polyethylene, synthetic foam, and composite.

13. The method for an inflatable bladder cast liner as in claim 8 further comprising the step of providing the circumferential edge2 with an edge lip bridge for bladder air flow to enter the fractured limb skin gap produced by the bladder fractured limb side inflated nipples.

14. The method for an inflatable bladder cast liner as in claim 8 further comprising the step of providing the inflatable bladder fractured limb skin side with an array of perforations.

\* \* \* \* \*